(12) United States Patent
Beswick et al.

(10) Patent No.: US 7,803,831 B2
(45) Date of Patent: Sep. 28, 2010

(54) 3-(2-HYDROXY-PHENYL)-1H-PYRAZOLE-4-CARBOXYLIC ACID AMIDE DERIVATIVES AS HSP90 INHIBITORS FOR THE TREATMENT OF CANCER

(75) Inventors: Mandy Christine Beswick, Harlow (GB); Paul Andrew Brough, Abington (GB); Martin James Drysdale, Abington (GB); Brian William Dymock, Abingdon (GB)

(73) Assignees: Vernalis (Cambridge) Limited (GB); Cancer Research Technology Ltd. (GB); Institute Of Cancer Research (GB)

( * ) Notice: Subject to any disclaimer, the term of this patent is extended or adjusted under 35 U.S.C. 154(b) by 962 days.

(21) Appl. No.: 10/536,898

(22) PCT Filed: Dec. 4, 2003

(86) PCT No.: PCT/GB03/05275

§ 371 (c)(1),
(2), (4) Date: Nov. 3, 2006

(87) PCT Pub. No.: WO2004/050087

PCT Pub. Date: Jun. 17, 2004

(65) Prior Publication Data

US 2007/0112192 A1    May 17, 2007

(30) Foreign Application Priority Data

Dec. 5, 2002  (GB) .................................. 0228417.2

(51) Int. Cl.
*A61K 31/415* (2006.01)
*A61K 31/4155* (2006.01)
*C07D 401/12* (2006.01)
*C07D 403/12* (2006.01)

(52) U.S. Cl. .................................... 514/406; 548/356.1
(58) Field of Classification Search ........................ None
See application file for complete search history.

(56) References Cited

FOREIGN PATENT DOCUMENTS

| EP | 0 656 354 A | 6/1995 |
| EP | 0656354 | 6/1995 |
| WO | 0236075 | 5/2002 |
| WO | WO 02 36075 A | 5/2002 |
| WO | 03055860 | 7/2003 |
| WO | WO 03 055860 A | 7/2003 |
| WO | 03072541 | 9/2003 |
| WO | WO 03 072541 A | 9/2003 |

*Primary Examiner*—Kamal A Saeed
(74) *Attorney, Agent, or Firm*—Banner & Witcoff, Ltd.

(57) ABSTRACT

Compounds of formula (IA) or (IB) or salts, N-oxides, hydrates or solvates thereof are Inhibitors of HSP90, and useful in the treatment of, for example, cancer: formula (IA), formula (IB) wherein Ar is an aryl or heteroaryl radical which is linked via a ring carbon, and which is substituted by a hydroxy group on a carbon in the 2-position, and which is otherwise either unsubstituted or optionally substituted; $R_1$ is hydrogen or optionally substituted $C_1$-$C_6$ alkyl; $R_2$ is hydrogen, optionally substituted cycloalkyl, cycloalkenyl, $C_1$-$C_6$ alkyl, $C_1$-$C_6$alkenyl, or $C_1$-$C_6$ alkynyl; or a carboxyl, carboxamide or carboxyl ester group; and $R_3$ is a carboxamide group.

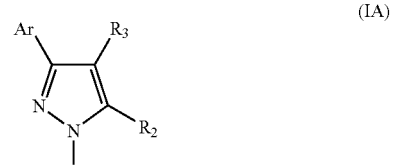

(IA)

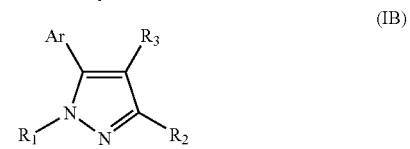

(IB)

18 Claims, No Drawings

3-(2-HYDROXY-PHENYL)-1H-PYRAZOLE-4-CARBOXYLIC ACID AMIDE DERIVATIVES AS HSP90 INHIBITORS FOR THE TREATMENT OF CANCER

This application is a U.S. National Stage application of co-pending PCT application PCT/GB2003/005275, filed Dec. 4, 2003, which claims the priority of Great Britain Patent Application No. 0228417.2, filed Dec. 5, 2002. These applications are incorporated herein by reference in their entireties.

This invention relates to substituted pyrazoles having HSP90 inhibitory activity, to the use of such compounds in medicine, in relation to diseases which are responsive to inhibition of HSP90 activity such as cancers, and to pharmaceutical compositions containing such compounds.

BACKGROUND TO THE INVENTION

Molecular chaperones maintain the appropriate folding and conformation of proteins and are crucial in regulating the balance between protein synthesis and degradation. They have been shown to be important in regulating many important cellular functions, such as cell proliferation and apoptosis (Jolly and Morimoto, 2000; Smith et al., 1998; Smith, 2001).

Heat Shock Proteins (HSPs)

Exposure of cells to a number of environmental stresses, including heat shock, alcohols, heavy metals and oxidative stress, results in the cellular accumulation of a number of chaperones, commonly known as heat shock proteins (HSPs). Induction of HSPs protects the cell against the initial stress insult, enhances recovery and leads to maintenance of a stress tolerant state. It has also become clear, however, that certain HSPs may also play a major molecular chaperone role under normal, stress-free conditions by regulating the correct folding, degradation, localization and function of a growing list of important cellular proteins.

A number of multigene families of HSPs exist, with individual gene products varying in cellular expression, function and localization. They are classified according to molecular weight, e.g., HSP70, HSP90, and HSP27.

Several diseases in humans can be acquired as a result of protein misfolding (reviewed in Tytell et al., 2001; Smith et al., 1998). Hence the development of therapies which disrupt the molecular chaperone machinery may prove to be beneficial. In some conditions (e.g., Alzheimer's disease, prion diseases and Huntington's disease), misfolded proteins can cause protein aggregation resulting in neurodegenerative disorders. Also, misfolded proteins may result in loss of wild type protein function, leading to deregulated molecular and physiological functions in the cell.

HSPs have also been implicated in cancer. For example, there is evidence of differential expression of HSPs which may relate to the stage of tumour progression (Martin et al., 2000; Conroy et al., 1996; Kawanishi et al., 1999; Jameel et al., 1992; Hoang et al., 2000; Lebeau et al., 1991). As a result of the involvement of HSP90 in various critical oncogenic pathways and the discovery that certain natural products with anticancer activity are targeting this molecular chaperone, the fascinating new concept has been developed that inhibiting HSP function may be useful in the treatment of cancer. The first molecular chaperone inhibitor is currently undergoing clinical trials.

HSP90

HSP90 constitutes about 1-2% of total cellular protein, and is usually present in the cell as a dimer in association with one of a number of other proteins (see, e.g., Pratt, 1997). It is essential for cell viability and it exhibits dual chaperone functions (Young et al., 2001). It plays a key role in the cellular stress response by interacting with many proteins after their native conformation has been altered by various environmental stresses, such as heat shock, ensuring adequate protein folding and preventing non-specific aggregation (Smith et al., 1998). In addition, recent results suggest that HSP90 may also play a role in buffering against the effects of mutation, presumably by correcting the inappropriate folding of mutant proteins (Rutherford and Lindquist, 1998). However, HSP90 also has an important regulatory role. Under normal physiological conditions, together with its endoplasmic reticulum homologue GRP94, HSP90 plays a housekeeping role in the cell, maintaining the conformational stability and maturation of several key client proteins. These can be subdivided into three groups: (a) steroid hormone receptors, (b) Ser/Thr or tyrosine kinases (e.g., ERBB2, RAF-1, CDK4, and LCK), and (c) a collection of apparently unrelated proteins, e.g., mutant p53 and the catalytic subunit of telomerase hTERT. All of these proteins play key regulatory roles in many physiological and biochemical processes in the cell. New HSP90 client proteins are continuously being identified.

The highly conserved HSP90 family in humans consists of four genes, namely the cytosolic HSP90α and HSP90β isoforms (Hickey et al., 1989), GRP94 in the endoplasmic reticulum (Argon et al., 1999) and HSP75/TRAP1 in the mitochondrial matrix (Felts et al., 2000). It is thought that all the family members have a similar mode of action, but bind to different client proteins depending on their localization within the cell. For example, ERBB2 is known to be a specific client protein of GRP94 (Argon et al., 1999) and type 1 tumour necrosis factor receptor (TNFR1) and RB have both been shown to be clients of TRAP1 (Song et al., 1995; Chen et al., 1996).

HSP90 participates in a series of complex interactions with a range of client and regulatory proteins (Smith, 2001). Although the precise molecular details remain to be elucidated, biochemical and X-ray crystallographic studies (Prodromou et al., 1997; Stebbins et al., 1997) carried out over the last few years have provided increasingly detailed insights into the chaperone function of HSP90.

Following earlier controversy on this issue, it is now clear that HSP90 is an ATP-dependent molecular chaperone (Prodromou et al, 1997), with dimerization of the nucleotide binding domains being essential for ATP hydrolysis, which is in turn essential for chaperone function (Prodromou et al, 2000a). Binding of ATP results in the formation of a toroidal dimer structure in which the N terminal domains are brought into closer contact with each other resulting in a conformational switch known as the 'clamp mechanism' (Prodromou and Pearl, 2000b).

Known HSP90 Inhibitors

The first class of HSP90 inhibitors to be discovered was the benzoquinone ansamycin class, which includes the compounds herbimycin A and geldanamycin. They were shown to reverse the malignant phenotype of fibroblasts transformed by the v-Src oncogene (Uehara et al., 1985), and subsequently to exhibit potent antitumour activity in both in vitro (Schulte et al., 1998) and in vivo animal models (Supko et al., 1995).

Immunoprecipitation and affinity matrix studies have shown that the major mechanism of action of geldanamycin involves binding to HSP90 (Whitesell et al., 1994; Schulte and Neckers, 1998). Moreover, X-ray crystallographic studies have shown that geldanamycin competes at the ATP binding site and inhibits the intrinsic ATPase activity of HSP90 (Prodromou et al., 1997; Panaretou et al., 1998). This in turn prevents the formation of mature multimeric HSP90 complexes capable of chaperoning client proteins. As a result, the client proteins are targeted for degradation via the ubiquitin proteasome pathway. 17-Allylamino, 17-demethoxygeldanamycin (17AAG) retains the property of HSP90 inhibition resulting in client protein depletion and antitumour activity in cell culture and xenograft models (Schulte et al, 1998; Kelland et al, 1999), but has significantly less hepatotoxicity than geldanamycin (Page et al, 1997). 17AAG is currently being evaluated in Phase I clinical trials.

Radicicol is a macrocyclic antibiotic shown to reverse the malignant phenotype of v-Src and v-Ha-Ras transformed fibroblasts (Kwon et al, 1992; Zhao et al, 1995). It was shown to degrade a number of signalling proteins as a consequence of HSP90 inhibition (Schulte et al., 1998). X-ray crystallographic data confirmed that radicicol also binds to the N terminal domain of HSP90 and inhibits the intrinsic ATPase activity (Roe et al., 1998). Radicicol lacks antitumour activity in vivo due to the unstable chemical nature of the compound.

Coumarin antibiotics are known to bind to bacterial DNA gyrase at an ATP binding site homologous to that of the HSP90. The coumarin, novobiocin, was shown to bind to the carboxy terminus of HSP90, i.e., at a different site to that occupied by the benzoquinone ansamycins and radicicol which bind at the N-terminus (Marcu et al., 2000b). However, this still resulted in inhibition of HSP90 function and degradation of a number of HSP90-chaperoned signalling proteins (Marcu et al., 2000a). Geldanamcyin cannot bind HSP90 subsequent to novobiocin; this suggests that some interaction between the N and C terminal domains must exist and is consistent with the view that both sites are important for HSP90 chaperone properties.

A purine-based HSP90 inhibitor, PU3, has been shown to result in the degradation of signalling molecules, including ERBB2, and to cause cell cycle arrest and differentiation in breast cancer cells (Chiosis et al., 2001).

HSP90 as a Therapeutic Target

Due to its involvement in regulating a number of signalling pathways that are crucially important in driving the phenotype of a tumour, and the discovery that certain bioactive natural products exert their effects via HSP90 activity, the molecular chaperone HSP90 is currently being assessed as a new target for anticancer drug development (Neckers et al., 1999).

The predominant mechanism of action of geldanamycin, 17AAG, and radicicol involves binding to HSP90 at the ATP binding site located in the N-terminal domain of the protein, leading to inhibition of the intrinsic ATPase activity of HSP90 (see, e.g., Prodromou et al., 1997; Stebbins et al., 1997; Panaretou et al., 1998).

Inhibition of HSP90 ATPase activity prevents recruitment of co-chaperones and encourages the formation of a type of HSP90 heterocomplex from which these client proteins are targeted for degradation via the ubiquitin proteasome pathway (see, e.g., Neckers et al., 1999; Kelland et al., 1999).

Treatment with HSP90 inhibitors leads to selective degradation of important proteins involved in cell proliferation, cell cycle regulation and apoptosis, processes which are fundamentally important in cancer.

Inhibition of HSP90 function has been shown to cause selective degradation of important signalling proteins involved in cell proliferation, cell cycle regulation and apoptosis, processes which are fundamentally important and which are commonly deregulated in cancer (see, e.g., Hostein et al., 2001). An attractive rationale for developing drugs against this target for use in the clinic is that by simultaneously depleting proteins associated with the transformed phenotype, one may obtain a strong antitumour effect and achieve a therapeutic advantage against cancer versus normal cells. These events downstream of HSP90 inhibition are believed to be responsible for the antitumour activity of HSP90 inhibitors in cell culture and animal models (see, e.g., Schulte et al., 1998; Kelland et al., 1999).

BRIEF DESCRIPTION OF THE INVENTION

The present invention makes available a new class of substituted pyrazole compounds, which are HSP90 inhibitors and which inhibit cancer cell proliferation. 2-Hydroxy aromatic substitution on one ring carbon atom and amido substitution on an adjacent ring carbon atom are principle characterising features of the compounds of the invention.

DETAILED DESCRIPTION OF THE INVENTION

According to the present invention there is provided a compound of formula (IA) or (IB) or a salt, N-oxide, hydrate or solvate thereof:

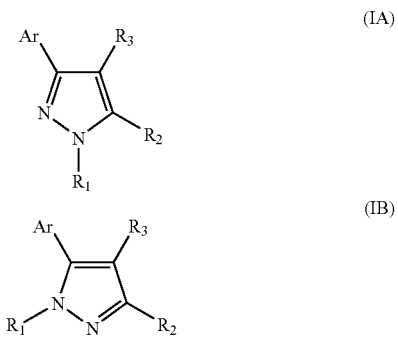

wherein

Ar is an aryl or heteroaryl radical which is linked via a ring carbon, and which is substituted by a hydroxy group on a carbon in the 2-position, and which is otherwise either unsubstituted or optionally substituted;

$R_1$ is hydrogen or optionally substituted $C_1$-$C_6$ alkyl;

$R_2$ is hydrogen, optionally substituted cycloalkyl, cycloalkenyl, $C_1$-$C_6$ alkyl, $C_1$-$C_6$ alkenyl, or $C_1$-$C_6$ alkynyl; or a carboxyl, carboxamide or carboxyl ester group; and $R_3$ is a carboxamide group.

When $R_1$ in compounds IA and IB is hydrogen, then compounds IA and IB are tautomeric forms of the same compound.

As used herein:

the term "carboxyl group" refers to a group of formula —COOH;

the term "carboxyl ester group" refers to a group of formula —COOR, wherein R is a radical actually or notionally derived from the hydroxyl compound ROH; and the term "carboxamide group" refers to a group of formula —CONR$_a$R$_b$, wherein —NR$_a$R$_b$ is a primary or secondary (including cyclic) amino group actually or notionally derived from ammonia or the amine HNR$_a$R$_b$.

As used herein, the term "(C$_1$-C$_6$)alkyl" refers to a straight or branched chain alkyl radical having from 1 to 6 carbon atoms, including for example, methyl, ethyl, n-propyl, iso-propyl, n-butyl, isobutyl, sec-butyl, t-butyl, n-pentyl and n-hexyl.

As used herein, the term "(C$_1$-C$_6$)alkenyl" refers to a straight or branched chain alkenyl radical having from 2 to 6 carbon atoms and containing at least one double bond of E or Z configuration, including for example, ethenyl and allyl.

As used herein, the term "(C$_1$-C$_6$)alkynyl" refers to a straight or branched chain alkenyl radical having from 2 to 6 carbon atoms and containing at least one triple bond, including for example, ethynyl and prop-2-ynyl.

As used herein the term "cycloalkyl" refers to a saturated carbocyclic radical having from 3-8 carbon atoms and includes, for example, cyclopropyl, cyclobutyl, cyclopentyl, cyclohexyl, cycloheptyl and cyclooctyl.

As used herein the term "cycloalkenyl" refers to a carbocyclic radical having from 3-8 carbon atoms containing at least one double bond, and includes, for example, cyclopentenyl, cyclohexenyl, cycloheptenyl and cyclooctenyl.

As used herein the term "aryl" refers to a mono-, bi- or tri-cyclic carbocyclic aromatic radical. Illustrative of such radicals are phenyl, biphenyl and napthyl.

As used herein the term "carbocyclic" refers to a cyclic radical whose ring atoms are all carbon, and includes monocyclic aryl, cycloalkyl and cycloalkenyl radicals.

As used herein the term "heteroaryl" refers to a mono-, bi- or tri-cyclic aromatic radical containing one or more heteroatoms selected from S, N and O. Illustrative of such radicals are thienyl, benzthienyl, furyl, benzfuryl, pyrrolyl, imidazolyl, benzimidazolyl, thiazolyl, benzthiazolyl, isothiazolyl, benzisothiazolyl, pyrazolyl, oxazolyl, benzoxazolyl, isoxazolyl, benzisoxazolyl, isothiazolyl, triazolyl, benztriazolyl, thiadiazolyl, oxadiazolyl, pyridinyl, pyridazinyl, pyrimidinyl, pyrazinyl, triazinyl, indolyl and indazolyl.

As used herein the unqualified term "heterocyclyl" or "heterocyclic" includes "heteroaryl" as defined above, and in particular means a mono-, bi- or tri-cyclic non-aromatic radical containing one or more heteroatoms selected from S, N and O, and to groups consisting of a monocyclic non-aromatic radical containing one or more such heteroatoms which is covalently linked to another such radical or to a monocyclic carbocyclic radical. Illustrative of such radicals are pyrrolyl, furanyl, thienyl, piperidinyl, imidazolyl, oxazolyl, isoxazolyl, thiazolyl, thiadiazolyl, pyrazolyl, pyridinyl, pyrrolidinyl, pyrimidinyl, morpholinyl, piperazinyl, indolyl, morpholinyl, benzfuranyl, pyranyl, isoxazolyl, benzimidazolyl, methylenedioxyphenyl, ethylenedioxyphenyl, maleimido and succinimido groups.

Unless otherwise specified in the context in which it occurs, the term "substituted" as applied to any moiety herein means substituted with up to four substituents, each of which independently may be, for example, (C$_1$-C$_6$)alkyl, (C$_1$-C$_6$)alkoxy, hydroxy, hydroxy(C$_1$-C$_6$)alkyl, mercapto, mercapto (C$_1$-C$_6$)alkyl, (C$_1$-C$_6$)alkylthio, halo (including fluoro and chloro), trifluoromethyl, trifluoromethoxy, nitro, nitrile (—CN), oxo, phenyl, —COOH, —COORA, —CORA, —SO$_2$R$^A$, —CONH$_2$, —SO$_2$NH$_2$, —CONHR$^A$, —SO$_2$NHR$^A$, —CONR$^A$R$^B$, —SO$_2$NR$^A$R$^B$, —NH$_2$, —NHR$^A$, —NR$^A$R$^B$, —OCONH$_2$, —OCONHR$^A$, —OCONR$^A$R$^B$, —NHCOR$^A$, —NHCOOR$^A$, —NR$^B$COOR$^A$, —NHSO$_2$OR$^A$, —NR$^B$SO$_2$OR$^A$, —NHCONH$_2$, —NR$^A$CONH$_2$, —NHCONHR$^B$, —NR$^A$CONHR, —NHCONR$^A$R$^B$, or —NR$^A$CONR$^A$R$^B$ wherein R$^A$ and R$^B$ are independently a (C$_1$-C$_6$)alkyl group.

As used herein the term "salt" includes base addition, acid addition and quaternary salts. Compounds of the invention which are acidic can form salts, including pharmaceutically or veterinarily acceptable salts, with bases such as alkali metal hydroxides, e.g. sodium and potassium hydroxides; alkaline earth metal hydroxides e.g. calcium, barium and magnesium hydroxides; with organic bases e.g. N-ethyl piperidine, dibenzylamine and the like. Those compounds (I) which are basic can form salts, including pharmaceutically or veterinarily acceptable salts with inorganic acids, e.g. with hydrohalic acids such as hydrochloric or hydrobromic acids, sulphuric acid, nitric acid or phosphoric acid and the like, and with organic acids e.g. with acetic, tartaric, succinic, fumaric, maleic, malic, salicylic, citric, methanesulphonic and p-toluene sulphonic acids and the like.

Some compounds of the invention contain one or more actual or potential chiral centres because of the presence of asymmetric carbon atoms. The presence of several asymmetric carbon atoms gives rise to a number of diastereoisomers with R or S stereochemistry at each chiral centre. The invention includes all such diastereoisomers and mixtures thereof.

In the compounds of the invention:

Ar may be, for example, a 2-hydroxyphenyl group which may be further substituted, for example by one or more of hydroxy, ethyl, isopropyl, chloro, bromo, or phenyl groups. Specifically, Ar may be a 2,4-dihydroxy-5-chlorophenyl group;

R$_1$ and R$_2$ may be, for example, hydrogen, methyl, ethyl, n- or iso-propyl, or hydroxyethyl. Hydrogen is presently preferred in the case of R$_1$, and hydrogen or methyl is presently preferred in the case of R$_2$;

R$_3$ may be, for example, a carboxamide group of formula —CONR$^B$(Alk)$_n$R$^A$ wherein Alk is a divalent alkylene, alkenylene or alkynylene radical, for example a —CH$_2$—, —CH$_2$CH$_2$—, —CH$_2$CH$_2$CH$_2$—, —CH$_2$CH=CH—, or —CH$_2$CCCH$_2$— radical, and the Alk radical may be optionally substituted, n is 0 or 1, R$^B$ is hydrogen or a C$_1$-C$_6$ alkyl or C$_2$-C$_6$ alkenyl group, for example methyl, ethyl, n- or iso-propyl, or allyl, R$^A$ is hydroxy or optionally substituted carbocyclic, for example optionally substituted phenyl; or heterocyclyl, for example pyridyl, furyl, thienyl, N-piperazinyl, or N-morpholinyl any of which heterocyclic rings may be substituted; optional substituents in any of the foregoing including OH, CH$_3$O—, Cl, F, NH$_2$CO—, NH$_2$CO—, CH$_3$NHCO— —COOH, —COOCH$_3$, —CH$_2$COOH, —CH$_2$COOCH$_3$, —CH$_3$, —CF$_3$, —SO$_2$CH$_3$, —SO$_2$NH$_2$, 3,4-methylenedioxy and 3,4-ethylenedioxy or R$^A$ and R$^B$ taken together with the nitrogen to which they are attached form an N-heterocyclic ring which may optionally contain one or more additional hetero atoms selected from O, S and N, and which may optionally be substituted on one or more ring C or N atoms, examples of such N-heterocyclic rings including morpholino, piperidinyl, piperazinyl and N-phenylpiperazinyl.

In a specific sub-class of compounds of the invention, R$_1$ and R$_2$ may be hydrogen, Ar may be a 2,4-dihydroxy-5-chlorophenyl group, Alk may be —CH$_2$—, n may be 0 or 1, R$^B$ may be hydrogen, and R$^A$ may be phenyl, optionally substituted by at least one of OH, CH$_3$O—, Cl, F, NH$_2$CO—, —COOH, —CH$_2$COOH, —CH$_3$, —CF$_3$, —SO$_2$CH$_3$ and 3,4-methylenedioxy.

Specific compounds of the invention include those of the Examples herein, particularly the following, and salts thereof:

3-(5-Chloro-2,4-dihydroxy-phenyl)-1H-pyrazole-4-carboxylic acid (4-acetyl-phenyl)-amide,
3-(5-Chloro-2,4-dihydroxy-phenyl)-1H-pyrazole-4-carboxylic acid phenyl amide,
3-(5-Chloro-2,4-dihydroxy-phenyl)-1H-pyrazole-4-carboxylic acid (4-methoxy-phenyl)-amide,
3-(5-Chloro-2,4-dihydroxy-phenyl)-1H-pyrazole-4-carboxylic acid (4-chloro-phenyl)-amide,
3-(5-Chloro-2,4-dihydroxy-phenyl)-1H-pyrazole-4-carboxylic acid (4-acetylamino-phenyl)-amide,
3-(5-Chloro-2,4-dihydroxy-phenyl)-1H-pyrazole-4-carboxylic acid 4-sulfamoyl-benzylamide,
3-(5-Chloro-2,4-dihydroxy-phenyl)-1H-pyrazole-4-carboxylic acid (4-methoxy-phenyl)-amide,
3-(5-Chloro-2,4-dihydroxy-phenyl)-1H-pyrazole-4-carboxylic acid (4-chloro-phenyl)-amide,
3-(5-Chloro-2,4-dihydroxy-phenyl)-1H-pyrazole-4-carboxylic acid (4-acetylamino-phenyl)-amide,
3-(5-Chloro-2,4-dihydroxy-phenyl)-1H-pyrazole-4-carboxylic acid 4-sulfamoyl-benzylamide,
3-(5-Chloro-2,4-dihydroxy-phenyl)-1H-pyrazole-4-carboxylic acid (4-carbamoyl-phenyl)-amide,
4-({[3-(5-Chloro-2,4-dihydroxy-phenyl)-1H-pyrazole-4-carbonyl]-amino}-methyl)-benzoic acid.
3-(5-Chloro-2,4-dihydroxy-phenyl)-1H-pyrazole-4-carboxylic acid 4-methyl-benzylamide,
3-(5-Chloro-2,4-dihydroxy-phenyl)-1H-pyrazole-4-carboxylic acid 4-methoxy-benzylamide,
3-(5-Chloro-2,4-dihydroxy-phenyl)-1H-pyrazole-4-carboxylic acid 4-fluoro-benzylamide,
3-(5-Chloro-2,4-dihydroxy-phenyl)-1H-pyrazole-4-carboxylic acid 4-chloro-benzylamide,
3-(5-Chloro-2,4-dihydroxy-phenyl)-1H-pyrazole-4-carboxylic acid 3-methoxy-benzylamide,
3-(5-Chloro-2,4-dihydroxy-phenyl)-1H-pyrazole-4-carboxylic acid 3-trifluoromethyl-benzylamide, and
3-(5-Chloro-2,4-dihydroxy-phenyl)-1H-pyrazole-4-carboxylic acid 4-methanesulfonyl-benzylamide.

Compounds of the invention may be prepared by amidation of a carboxylic acid of formula (IIA) or (IIB):

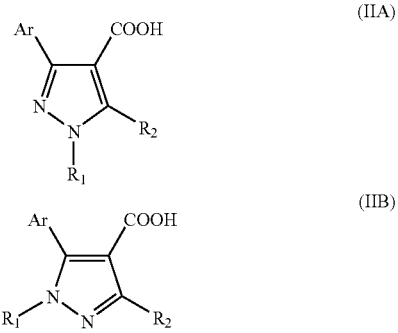

Typical reaction schemes and conditions for such amidation are set forth in the Examples herein.

The compounds of the invention are inhibitors of HSP90 and are thus useful in the treatment of diseases which are responsive to inhibition of HSP90 activity such as cancers; viral diseases such as Hepatitis C (HCV) (Waxman, 2002); Immunosupression such as in transplantation (Bijlmakers, 2000 and Yorgin, 2000); Anti-inflammatory diseases (Bucci, 2000) such as Rheumatoid arthritis, Asthma, MS, Type I Diabetes, Lupus, Psoriasis and Inflammatory Bowel Disease; Cystic fibrosis (Fuller, 2000); Angiogenesis-related diseases (Hur, 2002 and Kurebayashi, 2001): diabetic retinopathy, haemangiomas, psoriasis, endometriosis and tumour angiogenesis.

Accordingly, the invention also provides:
(i) a method of treatment of diseases or conditions responsive to inhibition of HSP90 activity in mammals, in particular in humans, which method comprises administering to the mammal an effective amount of a compound of formula (IA) or (IB) above; and
(ii) a compound of formula (IA) or (IB) above, for use in human or veterinary medicine, particularly in the treatment of diseases or conditions responsive to inhibition of HSP90 activity; and
(iii) the use of a compound of formula (IA) or (IB) above in the preparation of an agent for the management (by which is meant treatment or prophylaxis) of diseases or conditions responsive to inhibition of HSP90 activity.

It will be understood that the specific dose level for any particular patient will depend upon a variety of factors including the activity of the specific compound employed, the age, body weight, general health, sex, diet, time of administration, route of administration, rate of excretion, drug combination and the causative mechanism and severity of the particular disease undergoing therapy. In general, a suitable dose for orally administrable formulations will usually be in the range of 0.1 to 3000 mg once, twice or three times per day, or the equivalent daily amount administered by infusion or other routes. However, optimum dose levels and frequency of dosing will be determined by clinical trials as is conventional in the art.

The compounds with which the invention is concerned may be prepared for administration by any route consistent with their pharmacokinetic properties. The orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

The following examples illustrate the preparation and activities of specific compounds of the invention:

Scheme 1:

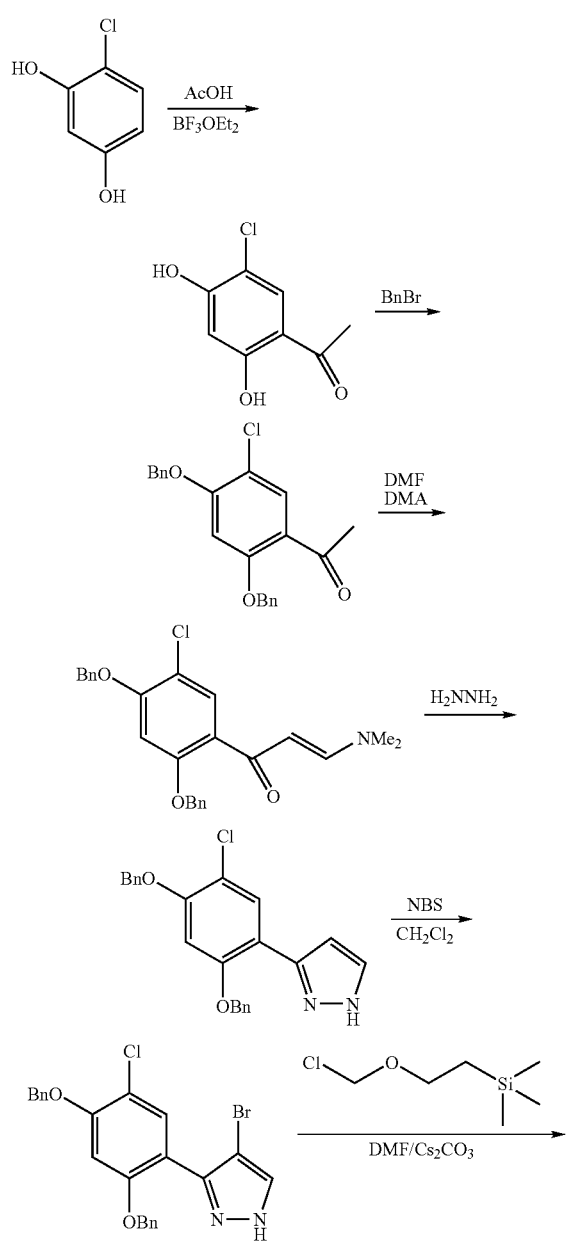

-continued

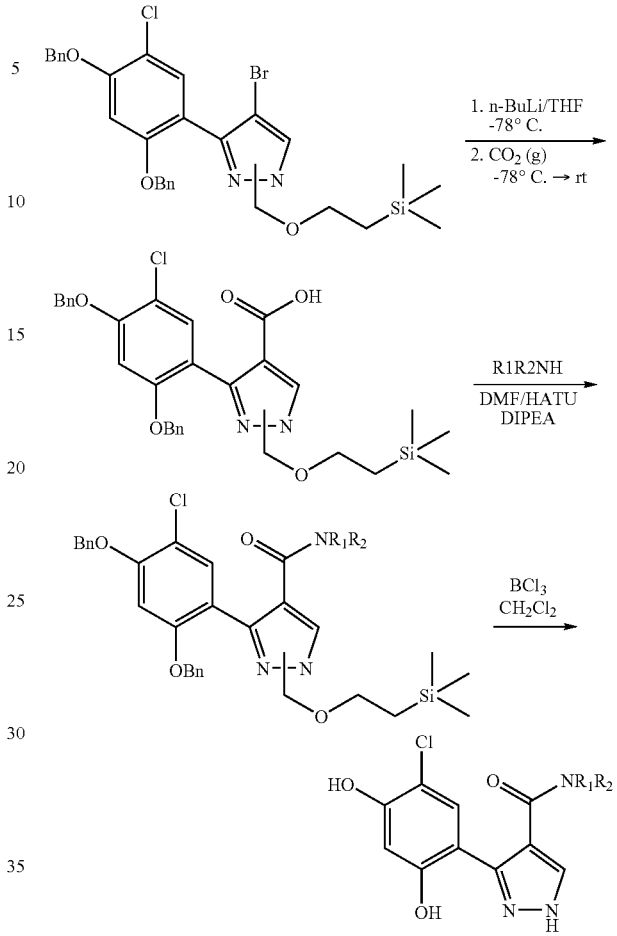

EXAMPLE 1

Step 1: 1-5-Chloro-2,4-dihydroxy-phenyl)-ethanone

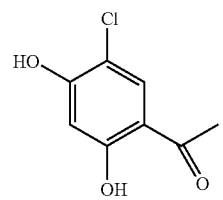

Acetic acid (17.5 mL) was added dropwise to a suspension of 4-chlororesorcinol (42.5 g, 0.293 mmol) in boron trifluoride etherate (200 mL) under a nitrogen atmosphere. The reaction mixture was heated at 90° C. for 3.5 hours and then allowed to cool to room temperature. A solid had formed after around 1 hour of cooling. The mixture was poured into 700 mL of a 10% w/v aqueous sodium acetate solution. This mixture was stirred vigorously for 2.5 hours. A light brown solid had formed which was filtered, washed with water and air-dried overnight to afford 1-(5-chloro-2,4-dihydroxy-phenyl)-ethanone (31.6 g, 58%). LCMS: [M-H]$^+$185.

Step 2: 1-(2,4-Bis-benzyloxy-5-chloro-phenyl)-ethanone

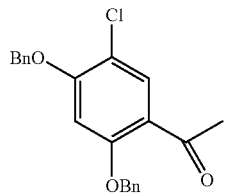

Benzyl bromide (30 mL) was added to a mixture of 1-(5-chloro-2,4-dihydroxy-phenyl)-ethanone (20 g, 0.107 moles) and potassium carbonate (37 g, 2.5 equiv) in acetonitrile (350 mL). The mixture was heated at reflux for 6 hours then allowed to cool and stirred overnight. The mixture was filtered and the solids were washed with dichloromethane (3×100 mL). The combined organic extracts were evaporated in vacuo to leave a pale yellow solid which was triturated with a mixture of hexane (350 mL)/ethyl acetate (15 mL) and filtered to give an off-white solid, 1-(2,4-bis-benzyloxy-5-chloro-phenyl)-ethanone (35.4 g, 90%). 1H NMR (400 MHz) consistent with structure.

Step3: 3-Amino-1-(2,4-bis-benzyloxy-5-chloro-phenyl)-propenone

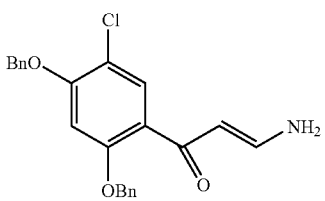

A solution of dimethylformamide dimethylacetal (13.5 mL, 1.1 equiv and 1-(2,4-bis-benzyloxy-5-chloro-phenyl)-ethanone (34 g, 0.09 moles) was heated to reflux at 150° C. for 2 hours. Another 10 mL of dimethylformamide dimethylacetal was added and heating continued for 3 hours. The mixture was allowed to cool and dimethylformamide was evaporated to leave an orange/red solid which was filtered and air-dried to afford 3-amino-1-(2,4-bis-benzyloxy-5-chloro-phenyl)-propenone (33 g, 84%).

LCMS: one component; [M+H]$^+$422, 424.

Step 4: 3-(2,4-Bis-benzyloxy-5-chloro-phenyl)-1H-pyrazole

Hydrazine hydrate (4.76 g, 1.1 equiv) was added to a suspension of 3-amino-1-(2,4-bis-benzyloxy-5-chloro-phenyl)-propenone(30.88 g, 0.07 moles) in ethanol (300 mL). The reaction mixture was heated to reflux for 4.5 hours then a further 200 mL of hydrazine was added and heating continued for 45 minutes. The mixture was allowed to cool to room temperature and stirred overnight. The off-white solid was filtered and washed with cold ethanol to afford 3-(2,4-bis-benzyloxy-5-chloro-phenyl)-1H-pyrazole (24 g). The filtrate was evaporated and the residue triturated with ethanol and filtered to give a further crop of 3-(2,4-bis-benzyloxy-5-chloro-phenyl)-1H-pyrazole (2.57 g). Total yield 92%. 1H NMR (400 MHz) consistent with structure.

Step 5: 3-(2,4-Bis-benzyloxy-5-chloro-phenyl)-4-bromo-1H-pyrazole

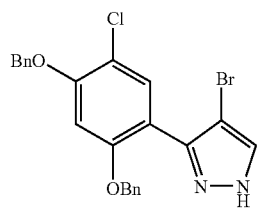

N-Bromosuccinimide (4.70 g, 26 mmol) was added in portions over 5 minutes to a stirred solution of 3-(2,4-Bis-benzyloxy-5-chloro-phenyl)-1H-pyrazole (10.29 g 26 mmol) in dichloromethane (200 ml). The reaction mixture was stirred at ambient temperature for 2 hours then water (200 ml) was added and vigorous stirring continued for 10 minutes. The phases were separated and the organic phase was washed with water (3×100 ml), saturated aqueous sodium chloride solution (2×100mi) and dried over sodium sulphate. The mixture was filtered and filtrate solvents were removed in vacuo to afford an off-white solid, which was triturated with ethyl acetate/hexane (1:20) mixture to give 3-(2,4-Bis-benzyloxy-5-chloro-phenyl)-4-bromo-1H-pyrazole (11.80 g, 97%) as off-white solid.

LC retention time 2.80 minutes [M+H]$^+$471, 469 (run time 3.75 mins).

Step 6: 3-(2,4-Bis-benzyloxy-5-chloro-phenyl)-4-bromo-1-(2-trimethylsilanyl-ethoxymethyl)-1H-pyrazole/3-(2,4Bis-benzyloxy-5-chloro-phenyl)-4-bromo-2-(2-trimethylsilanyl-ethoxymethyl)-1H-pyrazole

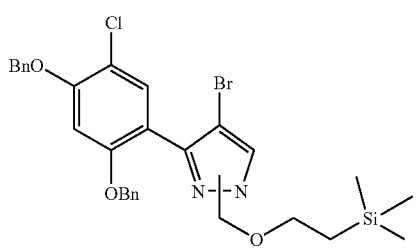

Cesium carbonate (16.3 g, 50 mmol) was added to a solution of 3-(2,4-Bis-benzyloxy-5-chloro-phenyl)-4-bromo-1H-pyrazole (11.80 g, 25 mmol) in DMF (70 ml). (2-Trimethylsilyl)ethoxymethyl chloride (4.93 ml, 32 mmol) was added in batches of ca. 500 μL over 4 hours and the mixture was stirred at ambient temperature for 16 hours. The majority of DMF was removed in vacuo and the residual mixture was partitioned between ethyl acetate (400 ml) and water (400 ml). The phases were separated and the organic phase was washed with water (2×250 ml), saturated aqueous sodium chloride solution (2×250 ml) and dried over sodium sulphate. The mixture was filtered and filtrate solvents were removed in vacuo to afford a yellow oil, which was purified by flash chromatography on silica gel (100 g) eluting with 5% ethyl acetate in hexane. This affords 3-(2,4-Bis-benzyloxy-5-chloro-phenyl)-4-bromo-1-(2-trimethylsilanyl-ethoxymethyl)-1H-pyrazole (15.0 g, 99%) as a pale yellow oil. $^1$H NMR analysis shows product is a mixture of regioisomers.

LC retention time 3.35 minutes [M+H]$^+$601, 599 (run time 3.75 mins).

Step 7: 3-(2,4-Bis-benzyloxy-5-chloro-phenyl-1-(2-trimethylsilanyl-ethoxymethyl)-1H-pyrazole-4-carboxylic acid/3-(2,4-Bis-benzyloxy-5-chloro-phenyl-2-(2-trimethylsilanyl-ethoxymethyl)-1H-pyrazole-4-carboxylic acid

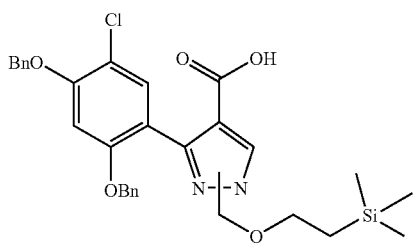

n-Butyl Lithium solution (1.6M, 7.8 ml, 12.4 mmol) was added drop-wise over 10 minutes to a −78° C. solution of 3-(2,4-Bis-benzyloxy-5-chloro-phenyl)-4-bromo-1-(2-trimethylsilanyl-ethoxymethyl)-1H-pyrazole (5.98 g, 9.97 mmol) in anhydrous THF (60 ml) under a Nitrogen atmosphere. The resulting orange-coloured solution was stirred at a −78° C. for 15 minutes then an excess of carbon dioxide gas was bubbled through the reaction mixture for two minutes (solution decolourises immediately). Cooling bath was removed and reaction mixture was allowed to warm to ambient temperature and quenched by addition of saturated aqueous ammonium chloride solution (100 ml). The reaction mixture was extracted with ethyl acetate (2×150 ml) and combined organic phases were washed with water (1×150 ml), saturated aqueous sodium chloride solution (2×250 ml) and dried over sodium sulphate. The mixture was filtered and filtrate solvents were removed in vacuo to afford a pale yellow solid which was re-crystallised from ethyl acetate hexane to afford 2.2 g of product as a colourless solid and as a mixture of regioisomers. The mother liquors from the crystallisation were evaporated in vacuo and the residual oil was purified by flash chromatography on silica gel (50 g) eluting with 10-50% ethyl acetate in hexane to give 0.316 g of product as a mixture of regioisomers. Total yield 2.516 g, (45%)

LC retention time 3.15 minutes [M+H]$^+$565 (run time 3.75 mins).

Step 8: 3-(5-Chloro-2,4dihydroxy-phenyl)-1H-pyrazole-4-carboxylic Acid (4-acetyl-phenyl)-amide

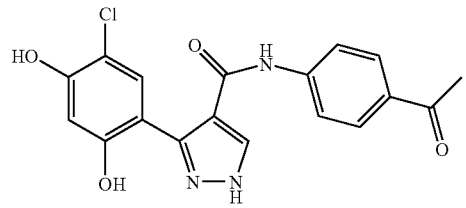

O-(7-Azabenzotriazol-yl)N,N,N',N'-tetramethyluronium hexafluorophosphate (100 mg, 0.27 mmol) was added to a mixture of 3-(2,4-Bis-benzyloxy-5-chloro-phenyl-1-(2-trimethylsilanyl-ethoxymethyl)-1H-pyrazole-4carboxylic acid and 3-(2,4-Bis-benzyloxy-5-chloro-phenyl-2-(2-trimethylsilanyl-ethoxymethyl)-1H-pyrazole-4-carboxylic acid (150 mg, 0.27 mmol). N,N-dimethylformamide (2.5 ml) was added, followed by 4-aminoacetophenone (43 mg, 0.32 mmol) and diisopropylethylamine (0.14 ml, 0.81 mmol). The reaction mixture was heated at 100° C. for 5 minutes using microwave heating and stood at ambient temperature for 2 hours. Solvents were removed in vacuo and the residue was partitioned between dichloromethane (8 ml) and aqueous sodium chloride solution (5 ml). Mixture was stirred vigorously for 10 minutes and the phases were separated. The organic phase was dried over anhydrous sodium sulphate and filtered and filtrate solvents were removed in vacuo to afford a brown oil. The crude amide product was re-dissolved in dichloromethane (2 ml) and placed under a nitrogen atmosphere. Boron trichloride (1.0M solution in dichloromethane, 1.35 ml, 1.35 mmol) was added drop-wise and a brown precipitate forms. Reaction mixture was stirred overnight then quenched by the cautious addition of saturated aqueous sodium bicarbonate solution (4 ml). Reaction mixture was extracted with ethyl acetate and phases separated. The organic phase was washed with brine then dried over sodium sulphate, filtered and filtrate solvents were removed in vacuo to afford brown solid which was purified by preparative HPLC to afford 3-(5-chloro-2,4-dihydroxy-phenyl)-1H-pyrazole-4-carboxylic acid (4-acetyl-phenyl)-amide (3 mg) as off-white solid.

LC retention time 1.97 minutes [M+H]$^+$372 (run time 3.75 mins).

The compound of Example 1 had an activity in the range "A" when tested in the malachite green assay described in the Biological Results section below.

The following further examples of compounds of the invention were prepared by methods analogous to the preparation of the compound of Example 1. In the following Table, the column headed "HSP90 IC50" contains the activity range of the compounds when tested in the malachite green assay described in the Biological Results section below.

| Example | Structure | MH+ | Hsp90 IC50 |
|---|---|---|---|
| 2 | 3-(5-chloro-2,4-dihydroxyphenyl)-N-phenyl-1H-pyrazole-4-carboxamide | 330 | B |
| 3 | (3-(5-chloro-2,4-dihydroxyphenyl)-1H-pyrazol-4-yl)(4-phenylpiperazin-1-yl)methanone | 400 | B |
| 4 | N-allyl-3-(5-chloro-2,4-dihydroxyphenyl)-1H-pyrazole-4-carboxamide | 294 | B |
| 5 | (3-(5-chloro-2,4-dihydroxyphenyl)-1H-pyrazol-4-yl)(morpholino)methanone | 324 | B |
| 6 | (3-(5-chloro-2,4-dihydroxyphenyl)-1H-pyrazol-4-yl)(4-methylpiperazin-1-yl)methanone | 337 | B |
| 7 | 3-(5-chloro-2,4-dihydroxyphenyl)-N-(3-morpholinopropyl)-1H-pyrazole-4-carboxamide | 381 | B |

-continued

| Example | Structure | MH+ | Hsp90 IC50 |
|---|---|---|---|
| 8 | 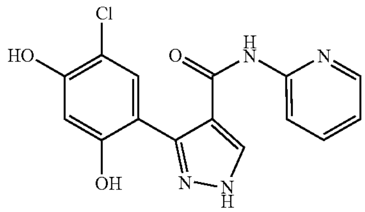 | 332 | B |
| 9 | 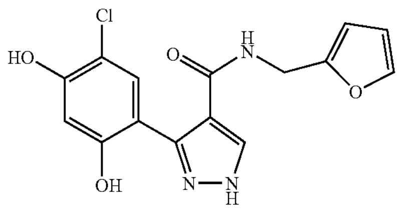 | 335 | A |
| 10 | 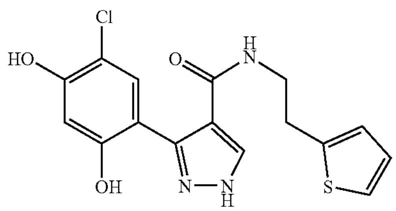 | 364 | A |
| 11 | 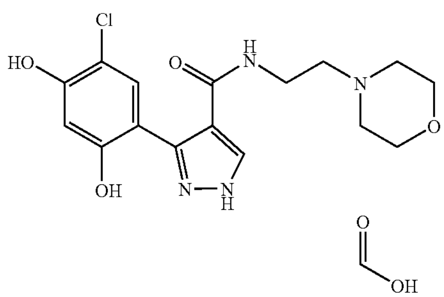 | 414 | B |
| 12 | 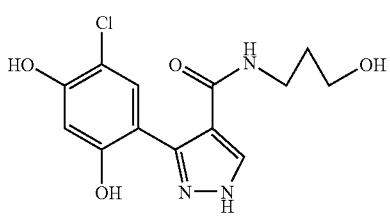 | 313 | B |
| 13 | 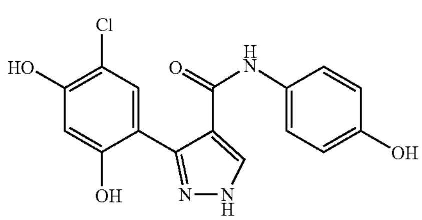 | 347 | A |

-continued

| Example | Structure | MH+ | Hsp90 IC50 |
|---|---|---|---|
| 14 | 3-(5-chloro-2,4-dihydroxyphenyl)-N-(3-methoxyphenyl)-1H-pyrazole-4-carboxamide | 361 | A |
| 15 | 3-(5-chloro-2,4-dihydroxyphenyl)-N-(2,3-dihydrobenzo[b][1,4]dioxin-6-yl)-1H-pyrazole-4-carboxamide | 389 | A |
| 16 | 3-(5-chloro-2,4-dihydroxyphenyl)-N-(3,4-dihydroxyphenyl)-1H-pyrazole-4-carboxamide | 363 | B |
| 17 | 3-(5-chloro-2,4-dihydroxyphenyl)-N-(4-methoxyphenyl)-1H-pyrazole-4-carboxamide | 361 | A |
| 18 | 3-(5-chloro-2,4-dihydroxyphenyl)-N-(4-chlorophenyl)-1H-pyrazole-4-carboxamide | 365 | B |
| 19 | N-(4-acetamidophenyl)-3-(5-chloro-2,4-dihydroxyphenyl)-1H-pyrazole-4-carboxamide | 388 | B |

-continued

| Example | Structure | MH+ | Hsp90 IC50 |
|---|---|---|---|
| 20 | 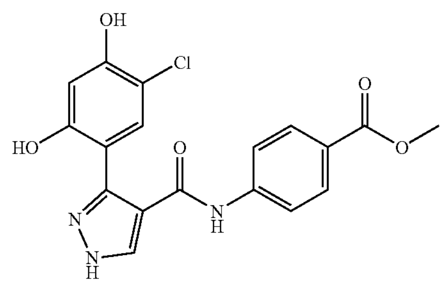 | 389 | A |
| 21 | 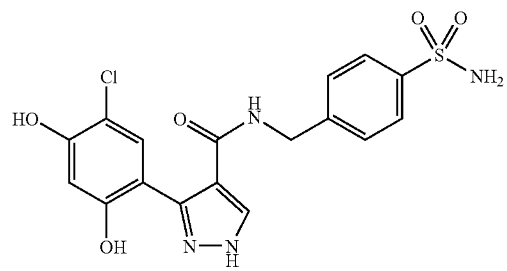 | 424 | A |
| 22 | 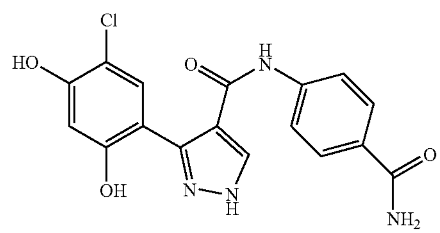 | 373 | A |
| 23 | 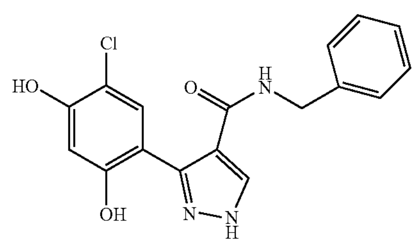 | 344 | B |
| 24 | 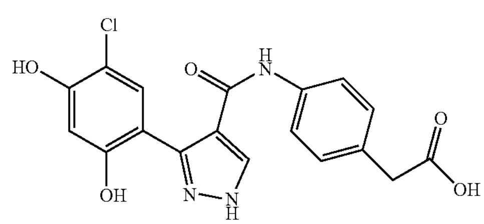 | 388 | B |
| 25 | 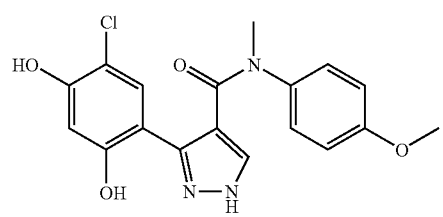 | 374 | B |

-continued

| Example | Structure | MH+ | Hsp90 IC50 |
|---|---|---|---|
| 26 | 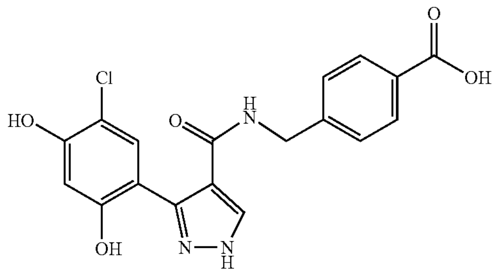 | 388 | A |
| 27 | 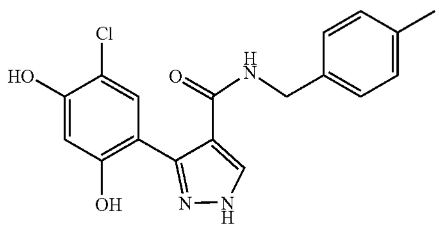 | 358 | A |
| 28 | 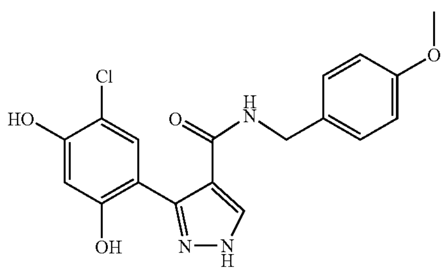 | 374 | A |
| 29 | 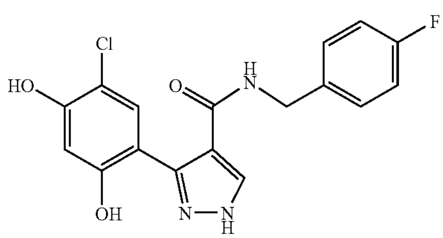 | 362 | A |
| 30 | 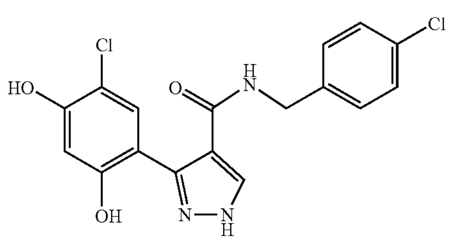 | 378 | A |
| 31 | 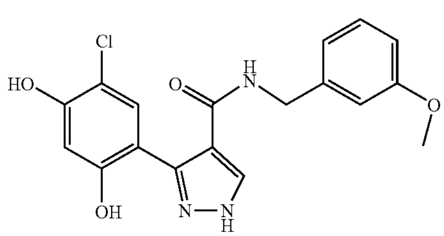 | 374 | A |

| Example | Structure | MH+ | Hsp90 IC50 |
|---|---|---|---|
| 32 | 3-(2,4-dihydroxy-5-chlorophenyl)-N-(3-trifluoromethylbenzyl)-1H-pyrazole-4-carboxamide | 412 | A |
| 33 | 3-(2,4-dihydroxy-5-chlorophenyl)-N-(4-methylsulfonylbenzyl)-1H-pyrazole-4-carboxamide | 422 | A |

Biological Results

The intrinsic ATPase activity of HSP90 may be measured using yeast HSP90 as a model system. The assay, based on the use of malachite green for the measurement of inorganic phosphate, was used to test the HSP90 inhibitory activity of the compounds of the Examples herein.

Malachite Green ATPase Assay

Materials

Chemicals are of the highest purity commercially available and all aqueous solutions are made up in AR water. Because of the need to minimise contamination with inorganic phosphate, precautions should be taken with solutions and apparatus used in the assays. Glassware and pH meters are rinsed with double distilled or deionised water before use and, wherever possible, plastic ware should be used. Gloves are worn for all procedures.

(1) Greiner 384-well (Greiner 781101) or Costar 384-well flat-bottomed polystyrene multiwell plates (VWR).
(2) Assay buffer of (a) 100 mM Tris-HCl, pH 7.4, (b) 150 mM KCl, (c) 6 mM $MgCl_2$. Stored at room temperature.
(3) 0.0812% (w/v) malachite green (M 9636, Sigma Aldrich Ltd., Poole, UK). Stored at room temperature.
(4) 2.32% (w/v) polyvinyl alcohol USP (P 1097, Sigma Aldrich Ltd, Poole, UK) in boiling water (see Comment 1), allowed to cool, and stored at room temperature.
(5) 5.72% (w/v) ammonium molybdate in 6 M hydrochloric acid. Stored at room temperature.
(6) 34% (w/v) sodium citrate. Stored at room temperature.
(7) 100 mM ATP, disodium salt, special quality (47699, Sigma Aldrich). Stored at −20° C.
(8) *E. coli* expressed yeast HSP90 protein, purified >95% (see, e.g., Panaretou et al., 1998) and stored in 50 uL aliquots at −80° C.

Method

1. Dilute test compounds to 500 μM in AR water (DMSO concentration will be 2.5%). Transfer 2.5 μl of these compounds directly from the daughter plate to the assay plate, giving a final assay concentration of 100 μM. To obtain 12 point IC50 values, perform serial dilutions 1:2 to produce a range of assay concentrations from 100 μM to 97.6 nM (2.5% DMSO), and transfer 2.5 μl of each concentration into the assay plate. Column 1 in the assay plate contains no compound, as a negative control. An additional row with no compound is also used as a background.
2. Prepare ATP by diluting 100 mM stock to 925 μM with assay buffer, and aliquot 5 μl of diluted ATP to each well including controls (final assay concentration 370 μM).
3. Add 5 μl of buffer to background row.
4. Dilute enzyme preparation to 1.05 μM with assay buffer, and aliquot 5 μl into each compound well and to the negative control column.
5. Collect the reagents to the bottom of the well, cover plate with plate seal and incubate overnight at 37 degC.
6. First thing in the morning prepare the Malachite Green Reagent. Add 2 parts of Malachite Green Solution, 1 part of Polyvinyl Alcohol Solution, 1 part of Ammonium Molybdate Solution, and 2 parts of AR water.
7. Invert to mix, and leave for approximately 1 hour until the colour turns from brown to golden yellow.
8. Add 40 μl of Malachite Green Reagent to each well, allow 5 mins for colour to develop.
9. Add 5 μl of Sodium Citrate Reagent to each well (see comment 2)
10. Re-cover with plate seal and shake on plate shaker for at least 15 mins.
11. Measure Absorbance at 620 nM using a suitable plate reader (e.g. Victor, Perkin Elmer Life Sciences, Milton Keynes, UK). Under these conditions, the control absorbance is 0.9 to 1.4, and the background is 0.2-0.35 giving a signal to noise ratio of ~12. The Z' factor calculated from data obtained using these conditions is between 0.6 and 0.9.

Comments (1) The polyvinyl alcohol dissolves in boiling water with difficulty and stirring for 2-3 h is required.

(2) The time interval between addition of the malachite green reagent and the sodium citrate should be kept as short as possible in order to reduce the non-enzymatic hydrolysis of ATP. Once the sodium citrate is added, the colour is stable for up to 4 h at room temperature.
(3) Compounds can be added to the assay plates using a Biomek FX Robot (Beckman Coulter). A Multidrop 384 dispenser (Thermo Labsystems, Basingstoke, UK) can be conveniently used to add reagents to the plate.
(4) The assay conditions were optimised with respect to time, protein and substrate concentration in order to achieve minimal protein concentration whilst retaining signal to noise differential.
(5) Signal to noise (S/N) is calculated using the following equation:

$$(S-B)/\sqrt{(SD \text{ of } S)^2 + (SD \text{ of } B)^2}$$

(6) To determine specific activity of HSP90, a range of inorganic phosphate concentrations (0-10 μM) are prepared and the absorbance at 620 nm measured as described. Specific activity is calculated from the resulting calibration curve.

The compounds tested in the above assay were assigned to one of two activity ranges, namely A=<50 μM; B=>50 μM, and those assignments are reported above.

A growth inhibition assay was also employed for the evaluation of candidate HSP90 inhibitors:

Assessment of Cytotoxicity by Sulforhodamine B (SRB) Assay: Calculation of 50% Inhibitory Concentration ($IC_{50}$).

Day 1
1) Determine cell number by haemocytometer.
2) Using an 8 channel multipipettor, add 160 μl of the cell suspension (3600 cells/well or $2 \times 10^4$ cells/ml) to each well of a 96-well microtitre plate.
3) Incubate overnight at 37° C. in a $CO_2$ incubator.

Day 2
4) Stock solutions of drugs are prepared, and serial dilutions of each drug are performed in medium to give final concentrations in wells.
5) Using a multipipettor, 40 μl of drug (at 5× final concentration) is added to quadruplicate wells.
6) Control wells are at either side of the 96 well plates, where 40 μl of medium is added.
7) Incubate plates in $CO_2$ incubator for 4 days (48 hours).

Day 6
8) Tip off medium into sink and immerse plate slowly into 10% ice cold trichloroacetic acid (TCA). Leave for about 30 mins on ice.
9) Wash plates three times in tap water by immersing the plates into baths of tap water and tipping it off.
10) Dry in incubator.
11) Add 100 μl of 0.4% SRB in 1%acetic acid to each well (except the last row (right hand)of the 96 well plate, this is the 0% control, ie no drug, no stain. The first row will be the 100% control with no drug, but with stain). Leave for 15 mins.
12) Wash off unbound SRB stain with four washes of 1% acetic acid.
13) Dry plates in incubator.
14) Solubilise SRB using 100 μl of 10 mM Tris base and put plates on plate shaker for 5 mins.
15) Determine absorbance at 540 nm using a plate reader. Calculate mean absorbance for quadruplicate wells and express as a percentage of value for control, untreated wells.
16) Plot % absorbance values versus log drug concentration and determine the $IC_{50}$.

The compound of Example 1 gave an IC50 in the 'B' range for the SRB growth arrest assay.

REFERENCES

A number of publications are cited above in order to more fully describe and disclose the invention and the state of the art to which the invention pertains. Full citations for these references are provided below. Each of these references is incorporated herein by reference in its entirety into the present disclosure.

Argon Y and Simen B B. 1999 "Grp94, an ER chaperone with protein and peptide binding properties", *Semin. Cell Dev. Biol.*, Vol. 10, pp. 495-505.

Bijlmakers M -J J E, Marsh M. 2000 "Hsp90 is essential for the synthesis and subsequent membrane association, but not the maintenance, of the Src-kinase p56lck", *Molecular Biology of the Cell*, Vol. 11 (5), pp. 1585-1595.

Bucci M; Roviezzo F; Cicala C; Sessa W C, Cirino G. 2000 "Geldanamycin, an inhibitor of heat shock protein 90 (Hsp90) mediated signal transduction has anti-inflammatory effects and interacts with glucocorticoid receptor in vivo", *Brit. J. Pharmacol.*, Vol 131(1), pp. 13-16.

Chen C -F, Chen Y, Dai K D, Chen P -L, Riley D J and Lee W -H. 1996 "A new member of the hsp90 family of molecular chaperones interacts with the retinoblastoma protein during mitosis and after heat shock", *Mol. Cell. Biol.*, Vol. 16, pp. 4691-4699.

Chiosis G, Timaul M N, Lucas B, Munster P N, Zheng F F, Sepp-Lozenzino L and Rosen N. 2001 "A small molecule designed to bind to the adenine nucleotide pocket of HSP90 causes Her2 degradation and the growth arrest and differentiation of breast cancer cells", *Chem. Biol.*, Vol. 8, pp. 289-299.

Conroy S E and Latchman D S. 1996 "Do heat shock proteins have a role in breast cancer?", *Brit. J. Cancer*, Vol. 74, pp. 717-721.

Felts S J, Owen B A L, Nguyen P, Trepel J, Donner D B and Toft D O. 2000 "The HSP90-related protein TRAP1 is a mitochondrial protein with distinct functional properties", *J. Biol. Chem.*, Vol. 5, pp. 3305-3312.

Fuller W, Cuthbert A W. 2000 "Post-translational disruption of the delta F508 cystic fibrosis transmembrane conductance regulator (CFTR)-molecular Chaperone complex with geldanamycin stabilizes delta F508 CFTR in the rabbit reticulocyte lysate", *J. Biol. Chem.*; Vol. 275(48), pp. 37462-37468.

Hickey E, Brandon S E, Smale G, Lloyd D and Weber L A. 1999 "Sequence and regulation of a gene encoding a human 89-kilodalton heat shock protein", *Mol. Cell. Biol.*, Vol. 9, pp. 2615-2626.

Hoang A T, Huang J, Rudra-Gonguly N, Zheng J, Powell W C, Rabindron S K, Wu C and Roy-Burman P. 2000 "A novel association between the human heat shock transcription factor I (HSF1) and prostate adenocarcinoma, *Am. J. Pathol.*, Vol. 156, pp. 857-864.

Hostein I, Robertson D, Di Stefano F, Workman P and Clarke P A. 2001 "Inhibition of signal transduction by the HSP90 inhibitor 17-allylamino-17-demethoxygeldanamycin results in cytostasis and apoptosis", *Cancer Res., Vol.* 61, pp. 4003-4009.

Hur E, Kim H -H, Choi SM, Kim J H, Yim S, Kwon H J, Choi Y, Kim D K, Lee M -O, Park H. 2002 "Reduction of hypoxia-induced transcription through the repression of hypoxia-inducible factor-1α/aryl hydrocarbon receptor nuclear translocator DNA binding by the 90-kDa heat-shock protein inhibitor radicicol", *Mol. Pharmacol.*, Vol 62(5), pp. 975-982.

Jameel A, Skilton R A, Campbell T A, Chander S K, Coombes R C and Luqmani Y A. 1992 "Clinical and biological significance of HSP89a in human breast cancer", *Int. J. Cancer*, Vol. 50, pp. 409-415.

Jolly C and Morimoto R I. 2000 "Role of the heat shock response and molecular chaperones in oncogenesis and cell death", *J. Natl. Cancer Inst.*, Vol. 92, pp. 1564-1572.

Kawanishi K, Shiozaki H, Doki Y, Sakita I, Inoue M, Yano M, Tsujinata T, Shamma A and Monden M. 1999 "Prognostic significance of heat shock proteins 27 and 70 in patients with squamous cell carcinoma of the esophagus", *Cancer*, Vol. 85, pp. 1649-1657.

Kelland L R, Abel G, McKeage M J, Jones M, Goddard P M, Valenti M, Murrer B A and Harrap K R. 1993 "Preclinical antitumour evaluation of bis-acetalo-amino-dichloro-cyclohexylamine platinum (IV): an orally active platinum drug", *Cancer Research*, Vol. 53, pp. 2581-2586.

Kelland L R, Sharp S Y, Rogers P M, Myers T G and Workman P. 1999 "DT-diaphorase expression and tumor cell sensitivity to 17-allylamino, 17-demethoxygeldanamycin, an inhibitor of heat shock protein 90", *J. Natl. Cancer Inst.*, Vol. 91, pp. 1940-1949.

Kurebayashi J, Otsuki T, Kurosumi M, Soga S, Akinaga S, Sonoo, H. 2001 "A radicicol derivative, KF58333, inhibits expression of hypoxia-inducible factor-1α and vascular endothelial growth factor, angiogenesis and growth of human breast cancer xenografts", *Jap. J. Cancer Res.*, Vol 92(12), 1342-1351.

Kwon H J, Yoshida M, Abe K, Horinouchi S and Bepple T. 1992 "Radicicol, an agent inducing the reversal of transformed phentoype of src-transformed fibroblasts, *Biosci., Biotechnol., Biochem., Vol.* 56, pp. 538-539.

Lebeau J, Le Cholony C, Prosperi M T and Goubin G. 1991 "Constitutive overexpression of 89 kDa heat shock protein gene in the HBL100 mammary cell line converted to a tumorigenic phenotype by the EJ/T24 Harvey-ras oncogene", *Oncogene*, Vol. 6, pp. 1125-1132.

Marcu MG, Chadli A, Bouhouche I, Catelli M and Neckers L. 2000a "The heat shock protein 90 antagonist novobiocin interacts with a previously unrecognized ATP-binding domain in the carboxyl terminus of the chaperone", *J. Biol. Chem.*, Vol. 275, pp. 37181-37186.

Marcu M G, Schulte T W and Neckers L. 2000b "Novobiocin and related coumarins and depletion of heat shock protein 90-dependent signaling proteins", *J. Natl. Cancer Inst.*, Vol. 92, pp. 242-248.

Martin K J, Kritzman BM, Price L M, Koh B, Kwan C P, Zhang X, MacKay A, O'Hare M J, Kaelin C M, Mutter G L, Pardee A B and Sager R. 2000 "Linking gene expression patterns to therapeutic groups in breast cancer", *Cancer Res.*, Vol. 60, pp. 2232-2238.

Neckers L, Schulte T W and Momnaaugh E. 1999 "Geldanamycin as a potential anti-cancer agent: its molecular target and biochemical activity", *Invest. New Drugs*, Vol. 17, pp. 361-373.

Page J, Heath J, Fulton R, Yalkowsky E, Tabibi E, Tomaszewski J, Smith A and Rodman L. 1997 ° "Comparison of geldanamycin (NSC-122750) and 17-allylaminogeldanamycin (NSC-330507D) toxicity in rats", *Proc. Am. Assoc. Cancer Res.*, Vol. 38, pp. 308.

Panaretou B, Prodromou C, Roe S M, O'Brien R, Ladbury J E, Piper P W and Pearl L H. 1998 "ATP binding and hydrolysis are essential to the function of the HSP90 molecular chaperone in vivo", *EMBO J.*, Vol. 17, pp. 4829-4836.

Pratt W B. 1997 "The role of the HSP90-based chaperone system in signal transduction by nuclear receptors and receptors signalling via MAP kinase", *Annu. Rev. Pharmacol. Toxicol.*, Vol. 37, pp. 297-326.

Prodromou C and Pearl L H. 2000a "Structure and in vivo function of HSP90", *Curr. Opin. Struct. Biol.*, Vol. 10, pp. 46-51.

Prodromou C, Roe S M, O'Brien R, Ladbury J E, Piper P W and Pearl L H. 1997 "Identification and structural characterization of the ATP/ADP-binding site in the HSP90 molecular chaperone", *Cell*, Vol. 90, pp. 65-75.

Prodromou C, Panaretou B, Chohan S, Siligardi G, O'Brien R, Ladbury J E, Roe S M, Piper P W and Pearl L H. 2000b "The ATPase cycle of HSP90 drives a molecular 'clamp' via transient dimerization of the N-terminal domains", *EMBO J.*, Vol. 19, pp. 4383-4392.

Roe S M, Prodromou C, O'Brien R, Ladbury J E, Piper P W and Pearl L H. 1999 "Structural basis for inhibition of the HSP90 molecular chaperone by the antitumour antibiotics radicicol and geldanamycin", *J. Med. Chem.*, Vol. 42, pp. 260-266.

Rutherford S L and Lindquist S. 1998 "HSP90 as a capacitor for morphological evolution. *Nature*, Vol. 396, pp. 336-342.

Schulte T W, Akinaga S, Murakata T, Agatsuma T, Sugimoto S, Nakano H, Lee Y S, Simen B B, Argon Y, Felts S, Toft D O, Neckers L M and Sharma S V. 1999 "Interaction of radicicol with members of the heat shock protein 90 family of molecular chaperones", *Mol. Endocrinology*, Vol. 13, pp. 1435-1448.

Schulte T W, Akinaga S, Soga S, Sullivan W, Sensgard B, Toft D and Neckers L M. 1998 "Antibiotic radicicol binds to the N-terminal domain of HSP90 and shares important biologic activities with geldanamcyin", *Cell Stress and Chaperones*, Vol. 3, pp. 100-108.

Schulte T W and Neckers L M. 1998 "The benzoquinone ansamycin 17:allylamino-17-deemthoxygeldanamcyin binds to HSP90 and shares important biologic activities with geldanamycin", *Cancer Chemother, Pharmacol.*, Vol. 42, pp. 273-279.

Smith D F. 2001 "Chaperones in signal transduction", in: *Molecular chaperones in the cell* (P Lund, ed.; Oxford University Press, Oxford and N.Y.), pp. 165-178.

Smith D F, Whitesell L and Katsanis E. 1998 "Molecular chaperones: Biology and prospects for pharmacological intervention", *Pharmacological Reviews*, Vol. 50, pp. 493-513.

Song H Y, Dunbar J D, Zhang Y X, Guo D and Donner D B. 1995 "Identification of a protein with homology to hsp9o that binds the type 1 tumour necrosis factor receptor", *J. Biol. Chem.*, Vol. 270, pp. 3574-3581.

Stebbins C E, Russo A, Schneider C, Rosen N, Hartl F U and Pavletich N P. 1997 "Crystal structure of an HSP90-geldanamcyin complex: targeting of a protein chaperone by an antitumor agent", *Cell*, Vol. 89, pp. 239-250.

Supko J G, Hickman R L, Grever M R and Malspeis L. 1995 "Preclinical pharmacologic evaluation of geldanamycin as an antitumour agent", *Cancer Chemother. Pharmacol.*, Vol. 36, pp. 305-315.

Tytell M and Hooper P L. 2001 "Heat shock proteins: new keys to the development of cytoprotective therapies", *Emerging Therapeutic Targets*, Vol. 5, pp. 267-287.

Uehara U, Hori M, Takeuchi T and Umezawa H. 1986 "Phenotypic change from transformed to normal induced by benzoquinoid ansamycins accompanies inactivation of p60src in rat kidney cells infected with Rous sarcoma virus", *Mol. Cell. Biol.*, Vol. 6, pp. 2198-2206.

Waxman, Lloyd H. Inhibiting hepatitis C virus processing and replication. (Merck & Co., Inc., USA). PCT Int. Appl. (2002), WO 0207761

Whitesell L, Mimnaugh E G, De Costa B, Myers C E and Neckers L M. 1994 "Inhibition of heat shock protein HSP90-pp60v-src heteroprotein complex formation by benzoquinone ansamycins: essential role for stress proteins in oncogenic transformation", *Proc. Natl. Acad. Sci. USA.*, Vol. 91, pp. 8324-8328.

Yorgin et al. 2000 "Effects of geldanamycin, a heat-shock protein 90-binding agent, on T cell function and T cell nonreceptor protein tyrosine kinases", *J. Immunol.*, Vol 164(6), pp. 2915-2923.

Young J C, Moarefi I and Hartl F U. 2001 "HSP90: a specialized but essential protein-folding tool", *J. Cell. Biol.*, Vol. 154, pp. 267-273.

Zhao J F, Nakano H and Sharma S. 1995 "Suppression of RAS and MOS transformation by radicicol", *Oncogene*, Vol. 11, pp. 161-173.

The invention claimed is:

1. A compound of formula (IA) or (IB) or a salt or N-oxide thereof:

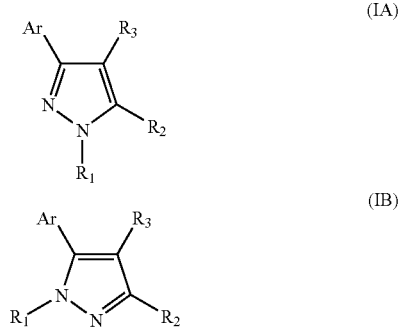

wherein

Ar is an aryl or heteroaryl radical which is linked via a ring carbon, and which is substituted by a hydroxy group on a carbon in the 2-position, and which is otherwise either unsubstituted or optionally substituted;

$R_1$ is hydrogen or optionally substituted $C_1$-$C_6$ alkyl;

$R_2$ is hydrogen, optionally substituted cycloalkyl, cycloalkenyl, $C_1$-$C_6$ alkyl, $C_1$-$C_6$ alkenyl, or $C_1$-$C_6$ alkynyl; or a carboxyl, carboxamide or carboxyl ester group; and;

$R_3$ is a carboxamide group.

2. A compound as claimed in claim 1 wherein Ar is a 2-hydroxyphenyl group which is optionally further substituted.

3. A compound as claimed in claim 1 wherein Ar is a 2-hydroxyphenyl group further substituted by one or more of hydroxy, ethyl, isopropyl, chloro, bromo, or phenyl groups.

4. A compound as claimed in claim 1 wherein Ar is a 2,4-dihydroxy-5-chlorophenyl group.

5. A compound as claimed in claim 1 wherein $R_1$ and $R_2$ are independently hydrogen, methyl, ethyl, n- or iso-propyl, or hydroxyethyl.

6. A compound as claimed claim 1 wherein $R_1$ is hydrogen and $R_2$ is hydrogen or methyl.

7. A compound as claimed claim 1 wherein $R_3$ is a carboxamide group of formula —$CONR^B(Alk)_nR^A$ wherein Alk is an optionally substituted divalent alkylene, alkenylene or alkynylene radical, n is 0 or 1, $R^B$ is hydrogen or a $C_1$-$C_6$ alkyl or $C_2$-$C_6$ alkenyl group $R^A$ is hydroxy or an optionally substituted carbocyclic or heterocyclic group.

8. A compound as claimed in claim 7 wherein Alk is —$CH_2$—, —$CH_2CH_2$—, —$CH_2CH_2CH_2$—, —$CH_2CH=CH$—, or —$CH_2CCCH_2$—, $R^B$ is hydrogen or methyl, ethyl, n-or iso-propyl, or allyl, and $R^A$ is hydroxy or optionally substituted phenyl, pyridyl, furyl, thienyl, N-piperazinyl, or N-morpholinyl.

9. A compound as claimed in claim 7 wherein $R^A$ is phenyl, optionally substituted by at least one of OH, $CH_3O$—, Cl, F, $NH_2CO$—, $NH_2CO$—, $CH_3NHCO$— —COOH, —$COOCH_3$, —$CH_2COOH$, —$CH_2COOCH_3$, —$CH_3$, —$CF_3$, —$SO_2CH_3$, —$SO_2NH_2$, 3,4-methylenedioxy and 3,4-ethylenedioxy.

10. A compound as claimed in any claim 7 wherein $R_1$ and $R_2$ are hydrogen, Ar is a 2,4-dihydroxy-5-chlorophenyl group, Alk is —$CH_2$—, n is 0 or 1, $R^B$ is hydrogen, and $R^A$ is phenyl, optionally substituted by at least one of OH, $CH_3O$—, Cl, F, $NH_2CO$—, $NH_2CO$—, $CH_3NHCO$—, —COOH, —$COOCH_3$, —$CH_2COOH$, —$CH_2COOCH_3$, —$CH_3$, —$CF_3$, —$SO_2CH_3$, —$SO_2NH_2$, 3,4-methylenedioxy and 3,4-ethylenedioxy.

11. A compound as claimed in claim 7 wherein $R^A$ and $R^B$ taken together with the nitrogen to which they are attached form an N-heterocyclic ring which optionally contains one or more additional hetero atoms selected from O, S and N, and which is optionally substituted on one or more ring C or N atoms.

12. A compound as claimed in claim 11 wherein $R^A$ and $R^B$ taken together with the nitrogen to which they are attached form amorpholino, piperidinyl, piperazinyl or N-phenylpiperazinyl ring, which is optionally substituted on one or more ring C or N atoms.

13. A compound as claimed in claim 1 selected from the group consisting of 3-(5-Chloro-2,4-dihydroxy-phenyl)-1H-pyrazole-4-carboxylic acid (4-acetyl-phenyl)-amide, 3-(5-Chloro-2,4-dihydroxy-phenyl)-1H-pyrazole-4-carboxylic acid phenyl-amide, 3-(5-Chloro-2,4-dihydroxy-phenyl)-1H-pyrazole-4-carboxylic acid (4-methoxy-phenyl)-amide, 3-(5-Chloro-2,4-dihydroxy-phenyl)-1H-pyrazole-4-carboxylic acid (4-chloro-phenyl)-amide, 3-(5-Chloro-2,4-dihydroxy-phenyl)-1H-pyrazole-4-carboxylic acid (4-acetylamino-phenyl)-amide, 3-(5-Chloro-2,4-dihydroxy-phenyl)-1H-pyrazole-4-carboxylic acid 4-sulfamoyl-benzylamide, 3-(5-Chloro-2,4-dihydroxy-phenyl)-1H-pyrazole-4-carboxylic acid (4-methoxy-phenyl)-amide, 3-(5-Chloro-2,4-dihydroxy-phenyl)-1H-pyrazole-4-carboxylic acid (4-chloro-phenyl)-amide, 3-(5-Chloro-2,4-dihydroxy-phenyl)-1H-pyrazole-4-carboxylic acid (4-acetylamino-phenyl)-amide, 3-(5-Chloro-2,4-dihydroxy-phenyl)-1H-pyrazole-4-carboxylic acid 4-sulfamoyl-benzylamide, 3-(5-Chloro-2,4-dihydroxy-phenyl)-1H-pyrazole-4-carboxylic acid (4-carbamoyl-phenyl)-amid, 4-({[3-(5-Chloro-2,4-dihydroxy-phenyl)-1H-pyrazole-4-carbonyl]-amino}=methyl)-benzoic acid, 3-(5-Chloro-2,4-dihydroxy-phenyl)-1H-pyrazole-4-carboxylic acid 4-methyl-benzylamide, 3-(5-Chloro-2,4-dihydroxy-phenyl)-1H-pyrazole-4-carboxylic acid 4-methoxy-benzylamide, 3-(5-Chloro-2,4-dihydroxy-phenyl)-1H-pyrazole-4-carboxylic acid 4-fluoro-benzylamide, 3-(5-Chloro-2,4-dihydroxy-phenyl)-1H-pyrazole-4-carboxylic acid 4-chloro-benzylamide, 3-(5-Chloro-2,4-dihydroxy-phenyl)-1H-pyrazole-4-carboxylic acid 3-methoxy-benzylamide, 3-(5-Chloro-2,4-dihydroxy-phenyl)-1H-pyrazole-4-carboxylic acid 3-trifluoromethyl-benzylamide, 3-(5-Chloro-2,4-dihydroxy-phenyl)-1H-pyrazole-4-carboxylic acid 4-methanesulfonyl-benzylamide, and salts and N-oxides thereof.

14. A method of treatment of diseases or conditions responsive to inhibition of HSP90 activity in mammals, comprising administering to the mammal an effective amount of a compound as claimed in claim 1.

15. A human or veterinary medicine comprising the compound as claimed in claim 1.

16. The medicine of claim 15 for the treatment of diseases or conditions responsive to inhibition of HSP90 activity.

17. A method as claimed in claim 14, wherein the disease or condition is a viral disease, transplant rejection, asthma, multiple sclerosis, Type I diabetes, lupus, psoriasis, inflammatory bowel disease, cystic fibrosis, diabetic retinopathy, haemangioma, or endometriosis.

18. A method as claimed in claim 14 wherein the mammals are humans.

* * * * *